United States Patent [19]

Highley

[11] 4,320,749
[45] Mar. 23, 1982

[54] APPARATUS FOR FACILITATING X-RAY EXAMINATIONS

[76] Inventor: Robert D. Highley, 18236-24th Ave. NE., Seattle, Wash. 98155

[21] Appl. No.: 218,617

[22] Filed: Dec. 22, 1980

[51] Int. Cl.³ .............................................. A61F 5/04
[52] U.S. Cl. .................................. 128/83; 128/84 R; 269/328
[58] Field of Search .................... 128/83, 84 R, 84 B, 128/84 C, 85, 87 R, 75, 80 R, 80 A, 80 G; 269/322, 328

[56] References Cited

U.S. PATENT DOCUMENTS

| | | | |
|---|---|---|---|
| 2,079,567 | 5/1937 | Anderson | 128/85 |
| 2,604,889 | 7/1952 | Erickson | 128/85 |
| 2,969,061 | 1/1961 | Sedlin | 128/84 R |
| 3,521,876 | 7/1970 | Smith | 269/328 |

Primary Examiner—John D. Yasko
Attorney, Agent, or Firm—Graybeal & Uhlir

[57] ABSTRACT

An apparatus (10) for determining by X-ray examination whether an anterior talo fibular ligament has been ruptured includes an angle-shaped support structure (12) having an upright member (14) attachable to the lower leg (L) of the patient. The support structure (12) also includes a base member (16) for slidably supporting a foot support carriage (18) for longitudinal movement toward and away from support member (14). Carriage (18) includes a heel wedge (20) for receiving the patient's heel (H). Straps (22) are provided for securing foot (F) to the top surface of carriage (18). A predetermined force is applied to heel (H) by a pneumatic loading system (26) designed to push carriage (18) forwardly in the coronal plane away from leg support member (14).

18 Claims, 6 Drawing Figures

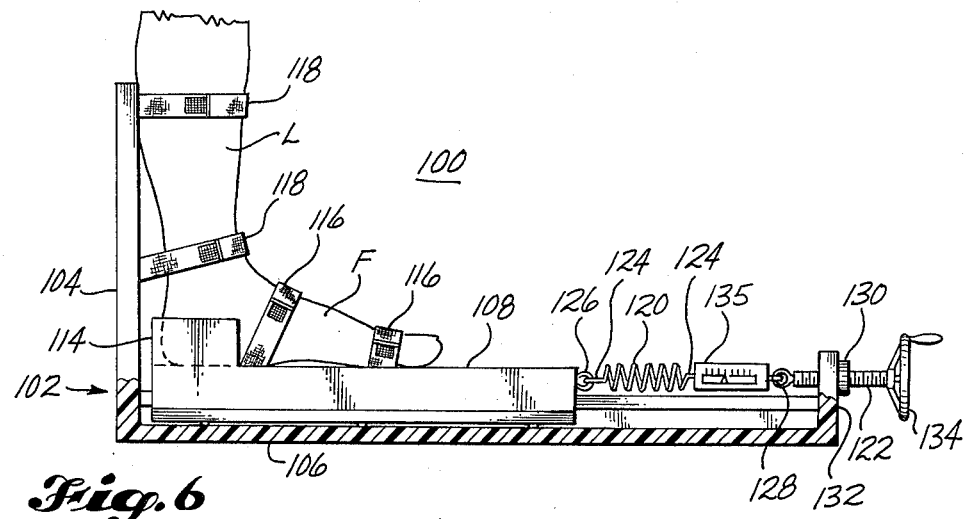
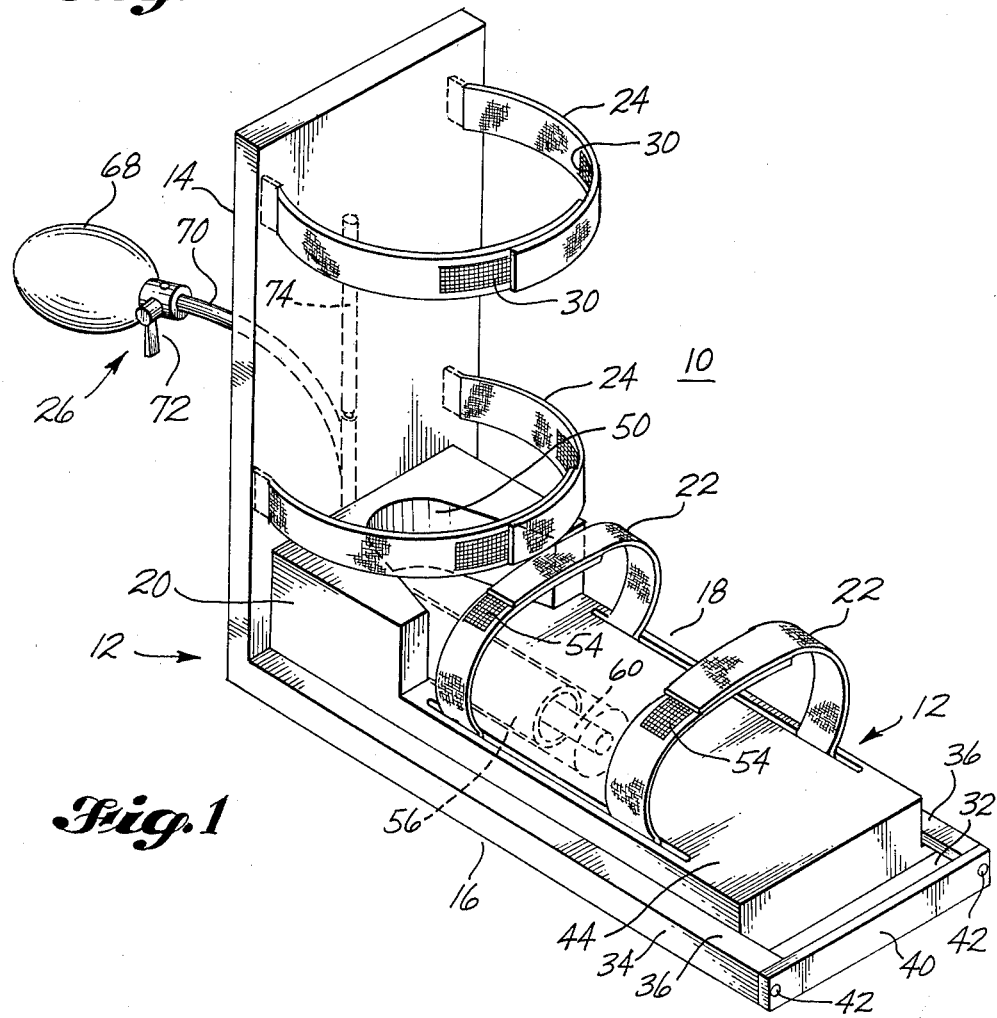

APPARATUS FOR FACILITATING X-RAY EXAMINATIONS

DESCRIPTION

Technical Field

The present invention relates to an apparatus for facilitating X-ray examinations of the human body, and more particularly to an apparatus for applying a controlled load on an ankle joint to diagnose the condition of the anterior talo-fibular ligament.

Background Art

With the increased participation in athletics by all segments of the population in recent years, a corresponding rise in bodily injuries has occurred. One of the most common types of injuries is to the ankle joint which is subjected to enormous strains and stresses during athletic activities. The ankle joint resembles a mortise joint with the lower portion of the tibia and fibula forming the mortise and the talus forming the tenon. The entire weight of the body is carried by the rather small articular surface of the ankle joint.

Normally the ankle joint is held in stable condition by ligaments which interconnect the talus with the tibia and fibula. When the ligaments are overstressed, such as when the ankle is severely twisted, the ankle ligaments may be damaged. The injury may be in the form of a ligament sprain or strain which is a partial tear of the ligament with some of the fibers still intact. A sprain injury is commonly treated by cooling the ankle area for a period of time. Also crutches may have to be used to avoid loading the injured ligament.

In a more serious situation, the ligament may tear completely, i.e. rupture. It is important that a rupture be properly diagnosed so that proper treatment occurs. The ruptured ligament may have to be sutured together and then a cast applied to the ankle area to allow proper healing of the ligament. In an alternative manner of treatment, a cast may be applied to the ankle without surgery.

A majority of ankle sprains and ruptures occur in the external colateral ligaments located at the lateral side of the ankle. By far the most commonly ruptured colateral ligament is the anterior talo-fibular ligament interconnecting the fibula and the front portion of the talus. The next most common rupture is to the calcaneo-fibular ligament which interconnects the tip of the malleolus with the lateral side of the calcaneous. With even less frequency the posterior talo-fibular ligament is ruptured.

Of the millions of ankle "sprains" seen by doctors annually in emergency rooms, approximately 13 percent of the injuries are not "sprains" as diagnosed, but in fact are ligament ruptures. Of these ruptures, approximately 80 percent occur to the anterior talo-fibular ligament itself. These misdiagnoses have been due, at least in part, to the lack of an accurate method and apparatus for isolating instances of anterior talo-fibular ligament rupture from instances of partial tearing or sprain of that ligament or the rupture or sprain of other ankle ligaments. There are in the prior art apparatuses for supporting the ankle area for an X-ray examination for rupture of the calcaneo-fibular ligament in combination with the rupture of the talo-fibular ligament. However, both the anterior talo-fibular and calcaneo-fibular ligaments rupture together in less than 10 percent of ankle ligament ruptures.

An example of an apparatus designed to support the ankle for X-ray examination of a combined anterior talo-fibular and calcaneo-fibular ligament rupture is disclosed in U.S. Pat. No. 3,521,876 wherein an upright foot support is adapted to pivot on a base plate. Transversely movable side blocks are carried by the foot support to press against the ankle bone. Also, a strap extends over the top of the foot to hold the foot to the foot support. The foot support is pivotable in one direction to evert the ankle to test whether the deltoid ligaments are ruptured and is pivotable in the opposite direction to invert the ankle to determine whether the calcaneo-fibular and anterior talo-fibular ligaments are ruptured. Because this particular apparatus is only capable of supporting the ankle during X-ray examinations through inversion and eversion, the apparatus is not capable of determining whether the anterior talo-fibular ligament alone has been ruptured.

U.S. Pat. No. 2,969,061 discloses another apparatus designed to support the ankle in inverted and everted positions during the taking of X-rays. The apparatus includes a pair of longitudinal angle members, one for each side of the foot. A pair of spaced apart connecting rods transversely interconnect the end portions of the angle members so that the width separating the angle plates can be adjusted to press the plates against the sides of the foot. A tie strap is provided for extending around the thigh and a traction rope extends from a loop formed in the tie strap to the ends of the connecting rods. As the traction rope is tightened the foot is tilted sideways and held in such position for X-ray examination of the ankle area.

The presently used technique for supporting the ankle during an X-ray examination to test for the rupture of the anterior talo-fibular ligament is to manually grasp the rear of the heel and exert a forward force on the heel while holding the lower leg stationary. This manual technique is not only difficult to perform, but also subjects the operator's hands to repeated exposure to X-rays which eventually could cause adverse effects to the operator's health. Moreover, pulling on the heel by hand makes it very difficult to exert a precise force on the heel. It is possible that an overzealous tester may in fact cause additional injury to the ligaments by overloading the ankle joint.

Disclosure of Invention

The present invention relates to an apparatus for accurately imposing a predetermined load on an ankle joint in the coronal plane so that an X-ray examination can be made to determine whether the anterior talo-fibular ligament has ruptured. The apparatus includes an angle-shaped support structure having a first member which is securable to the patient's lower leg through the use of a pair of straps. The base member of the support structure extends transversely from the lower end of the support member forwardly of the patient's foot. A foot support carriage is supported by the base member for movement transversely toward and away from the support member. A heal wedge is affixed to the end of the carriage adjacent the support member for pushing forwardly against the heel of the foot. Grooves are formed in the side portions of the support structure base member for slidably receiving corresponding flanges formed along the sides of the carriage to thereby guide the carriage for movement toward and away from the support member while preventing transverse movement of the carriage relative to the length of the base member.

An elongate cylinder extends transversely forward from the lower end of the support member into a clearance bore formed in the carriage. A piston is fixed to the free end of an elongate piston rod extending rearwardly from an intermediate portion of the carriage to slidably engage within the cylinder. An expandable bladder is disposed within the cylinder so that when the bladder is enlarged it presses against the piston to slide the carriage transversely away from the support member to in turn push forwardly against the patient's heel. A squeeze ball is provided for pressurizing the bladder and a manometer is connected in fluid communication with the bladder to measure the pressure of the working fluid within the bladder so that a predetermined low level, forwardly directed, force can be applied to the heel. If the anterior talo-fibular ligament is ruptured, the force applied to the heel will case the talus to displace forwardly of the fibular, which forward displacement will be visible in the X-ray photographs.

The present invention has the advantage that a precise predetermined load can be applied to the patient's heel in the proper direction to determine through X-ray examination whether the anterior talo-fibular alignment has been ruptured without subjecting medical personnel to X-ray exposure. Moreover, the present invention limits the magnitude of the load applied to the heel so that further injury to the ankle ligaments is avoided.

BRIEF DESCRIPTION OF THE DRAWINGS

The details of the present invention will be described in connection with the accompanying drawings, in which:

FIG. 1 is an isometric view of a typical apparatus constructed according to the present invention for facilitating X-ray examinations of a patient's ankle ligaments;

FIG. 6 is a partially schematic side elevational view of another typical embodiment of the present invention.

BEST MODE OF THE INVENTION

Figure 2:
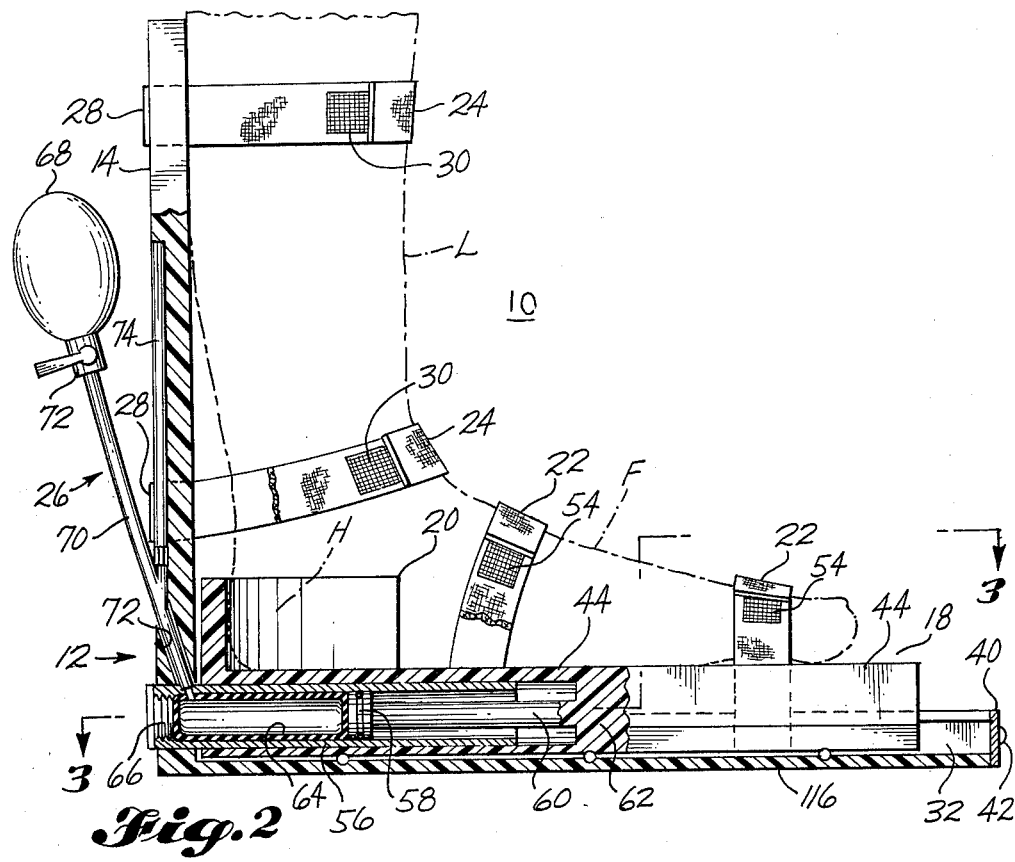
FIG. 2 is a side elevational view of the typical apparatus illustrated in FIG. 1 with portions broken away to illustrate the expandable bladder.
Figure 3:
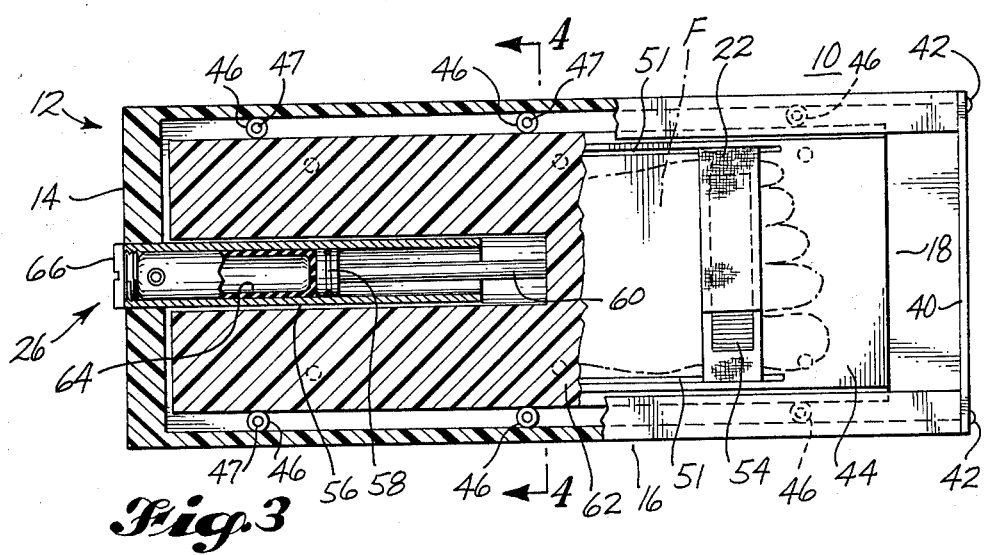
FIG. 3 is a cross-sectional view of the typical apparatus illustrated in FIG. 2, taken substantially along lines 3—3 thereof.

Referring initially to FIG. 2, a lower leg L and foot F of a patient are illustrated as secured to an apparatus 10 constructed according to the best mode of the present invention for facilitating X-ray examinations of ankle ligament injuries. Additionally, referring to FIGS. 3 and 4, apparatus 10 is shown to include an angle-shaped support structure 12 composed of a leg support member 14 extending tranversely upwardly from one end of a base member 16. An elongate, foot support carriage 18 is adapted to artifrictionally slide along the length of base member 16 in a direction transverse to support member 14. Carriage 18 includes a heel wedge 20 for receiving the heel portion H of foot F. A pair of straps 22 are provided for securing foot F to carriage 18 and a second pair of straps 24 are provided for securing the lower leg L to support member 14. A pneumatic loading system 26 pushes carriage 18 forwardly away from leg support member 14 to thereby push heel H forward relative to lower leg L. If the patient's anterior talo-fibular ligament is ruptured, this forward load on heel H will cause displacement of the talus from the lateral malleolus of the fibula, which displacement will be visible in an X-ray photograph. If the anterior talo-fibular ligament is in fact ruptured, proper treatment can be prescribed for this injury, which treatment is significantly different than the standard treatment for a sprained ligament.

Support structure 12 includes an upright support member 14 extending upwardly to the elevation of the patient's calf. For simplicity of construction, support member 14 is preferably in the form of a flat plate; however, if desired, member 14 may be contoured to more closely correspond to the shape of leg L. A pair of vertically spaced straps 24 extend forwardly from support member 14 to wrap around lower leg L to thereby securely hold lower leg L stationary relative to the support member. Straps 24 extend through slots formed within support member 24. Each strap is composed of two halves with a bead member 28 formed at the end of each half of a thickness thicker than the strap itself to prevent the strap half from disengaging from its corresponding support member slot. Velcro tabs 30 are attached to the free ends of the strap halves to lock the straps tightly around lower leg L. Rather than using Velcro tabs 30, straps 24 can be fitted with a buckle or other conventional device for attaching the free ends of the strap halves together.

Support structure 12 also includes an elongate base member 16 extending transversely forward from the lower end portion of support member 14. Although not essentially required, base member 16 is illustrated as having a width equal to that of support member 14. The length of base member 16 is ideally somewhat longer than carriage 18 to thereby accommodate the longitudinal movement of the carriage. As perhaps most clearly illustratd in FIG. 4, base member 16 includes a flat bottom plate 32 and a pair of upright side walls 34 extending upwardly from the side edge portions of plate 32. Base member 16 also includes a relatively narrow top wall 36 extending transversely inwardly from the upper edge of each side wall 34 toward the longitudinal center of the base member. Top all 36, side wall 34 and adjacent edge portion of bottom plate 32 cooperate together to form a rectangularly shaped slot 38 extending longitudinally along each side portion of base member 16. Slots 38 are open in the direction facing the longitudinal center of base member 16.

As illustrated in FIGS. 1-4, carriage 18 is generally rectangular in shape, having a width slightly narrower than base member 16 and a length somewhat shorter than the length of the base member. Carriage 18 includes a rectangularly shaped bed 44 on which foot F rests. Additionally, referring to FIG. 5, a flange member 45 extends transversely outwardly from the lower edge portion of each side of bed 44 to closely and slidably engage within a corresponding slot 36 formed within base member 16. A plurality of rollers 46 are mounted on vertical axles 47 spanning between base member top wall 36 and bottom plate 32. Rollers ride against the side edges of flanges 45. This particular construction enables carriage 18 to antifrictionally slide longitudinally along base member 16 while constraining the carriage from transverse movement relative to base member 16. It is to be understood that rather than being constructed in the above manner, base member 16 may be formed with flanges such as carriage flanges 45; and carriage 18 may be formed with a pair of longitudinal slots and rollers, such as slots 38 and rollers 46. Although not essentially required, to further enhance the antifrictional longitudinal movement of carriage 18, ideally the lower surface of bed 44 is spaced slightly above the upper surface of base member bottom plate 32 by a plurality of spherical rollers 48. The upper portion of rollers 48 are disposed within semispherically-shaped pockets formed in bed 44 while the lower portion of the rollers are disposed within corresponding semispherically-shaped pockets formed in bottom plate 32.

Carriage 18 includes a heel abutment member in the form of wedge 20 extending upwardly from the end portion of carriage top plate 44 adjacent support member 14. Ideally, the width of wedge member 20 corresponds to the width of carriage 18 to thereby form an upwardly extending continuation of this portion of the carriage. Wedge 20 is formed in a generally V-shape to define a forwardly open slot 50 for receiving the heel portion H of foot F. The base of slot 50 abuts against the back of heel H while the sides of the slot laterally support and constrain heel H.

Figure 4:
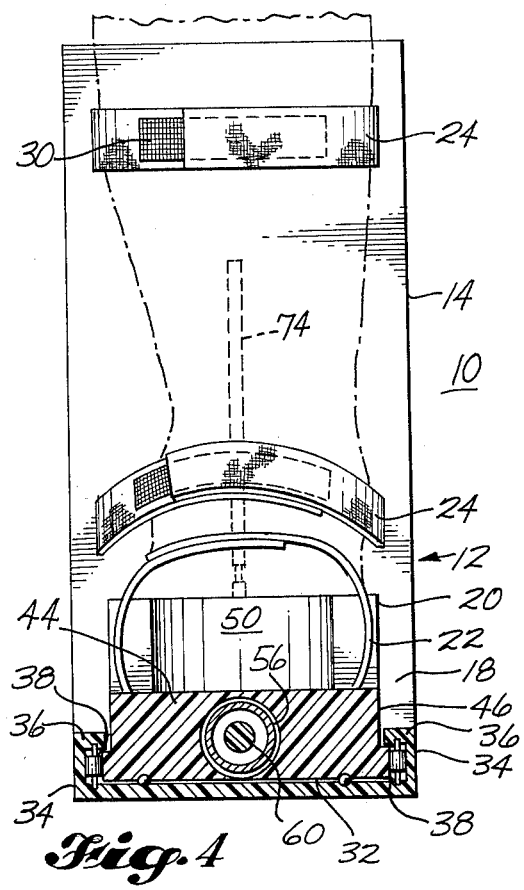
FIG. 4 is a partially schematic cross-sectional view of the typical apparatus illustrated in FIGS. 1-3, taken substantially along lines 4—4 of FIG. 3.
Figure 5:
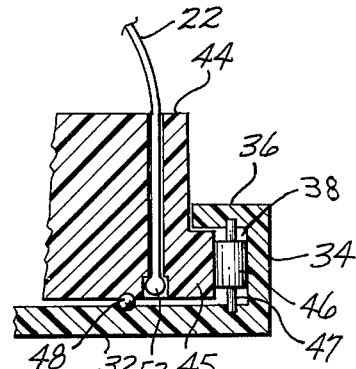
FIG. 5 is an enlarged fragmentary, partially schematic cross-sectional view of the typical apparatus illustrated in FIG. 4 specifically depicting the carriage rollers.

Foot F is further secured to carriage 18 by a pair of straps 22 extending upwardly from carriage top plate 44. As best shown in FIG. 4, each strap 22 includes two halves with each half engageable within an elongate slot 51 formed in carriage bed 44. Each slot 51 includes an enlarged lower portion 52 to receive a bead member 53 formed in the end of each strap half. Bead member 52 is thicker than strap 22 itself to prevent disengagement of the strap halves from their corresponding slots but smaller in diameter than the depth of slot lower portion 52 to avoid any interference between the bead member and the upper surface of base member bottom plate 32. Velcro tabs 54, or other conventional means, are affixed to the free end portions of straps 22 to hold the strap halves together over foot F. Straps 22 may be longitudinally slid along slots 51 to position the rearward strap adjacent the patient's heel and the forward strap near the front of the patient's foot.

Apparatus 10 of the present invention also includes a pneumatic loading system 26 for applying a forwardly directed load in the coronal plane on carriage 28. Loading system 26 includes an elongate, circular cylinder 56 extending transversely forward from the lower edge portion of support member 14 in alignment with the direction of travel of carriage 18 to extend within a clearance bore 57 formed within bed 44. The forward or free end of cylinder 56 terminates at approximately the longitudinally medial region of the carriage. Cylinder 56 is fixedly attached to support member 14 by any convenient means, such as by welding to lie generally centrally within bore 56 to thereby avoid creating any impediment to the free travel of carriage 18 along base member 16.

The inside diameter of cylinder 56 is sized to slidably receive a piston 58 affixed to the rear or free end of an elongate piston rod 60 extending rearwardly from a central portion 62 of carriage 18. An expandable bladder 64 is disposed within cylinder 56 between piston 58 and a plug 66 which is threadably engaged within the end portion of cylinder 56 adjacent leg support member 14. Bladder 64 is expandable in the longitudinal direction when pressurized by a working fluid, i.e. air, to thereby force carriage 18 along the length of base member 16 away from leg support member 14 to exert a forwardly directed force on the back of heel H. Ideally, bladder 64 is constructed from flexible material, such as rubber.

Pressurized air is supplied to bladder 64 by a pressure source such as a squeeze bulb 68 which is interconnected in fluid flow communication with bladder 64 by flexible line 70, which extends through a diagonal passageway 72 formed in support member 14 and cylinder 56. When bulb 68 is squeezed, the pressurized air expands bladder 64 to force the bladder against piston 58. Ideally, bulb 68 is fitted with a pressure relief valve, not shown, which limits the maximum pressure of the air within bladder 64 to thereby limit the force imposed on heel H to approximately 12 pounds. A manually operable pressure release valve 73 is located at the connection between bulb 68 and line 70 to release the pressure within bladder 64 to thereby permit carriage 18 to return to its retracted position illustrated in FIGS. 1–3.

Rather than utilizing bladder 64, a conventional, airtight, cylinder and piston could be used. Moreover, rather than using air, hydraulic fluid can be used as the working fluid, in which case the hydraulic fluid can be stored within bulb 68 itself or within an additional storage receptacle attached to the back side of leg support member 14, i.e. on the side opposite lower leg L.

A manometer 74, connected in fluid flow communication with line 70, extends upwardly along the back side of leg support member 14. Manometer 74 can be calibrated to indicate in pounds the force being applied to heel H by heel wedge 20. This enables the operator to place a precise load on heel H and thereby avoid overloading the ankle joint and causing further damage to the ankle ligament.

To utilize apparatus 10, a patient's foot F is initially placed on carriage 18 with heel H pushed rearwardly against wedge 20. Thereafter, carriage straps 22 are fastened together over the top of foot F and straps 24 are placed around lower leg L to securely press the back of the lower leg against leg support member 14. Normally, the patient will be lying on his side so that support structure 12 is disposed sideways rather than being upright as shown in FIGS. 1–5.

Next, bladder 64 is pressurized to a predetermined level so that a selective force, such as twelve pounds, is applied to heel H by wedge 20. X-rays of the ankle area are taken when the ankle is thusly loaded to determine whether or not the anterior talo-fibular ligament is in fact ruptured. It will be appreciated that during this procedure no part of the operator's body is exposed to X-rays, since the patient's foot and leg are entirely supported by apparatus 10 and not by the operator.

An alternative embodiment of the present invention is illustratd in FIG. 6 wherein another apparatus 100 for facilitating X-ray examinations of an ankle joint includes a generally angle-shaped support structure 102 having an upright leg support member 104 and an elongate base member 106 extending transversely forwardly from the lower end of support member 104. A foot support carriage 108 is slidably mounted on base member 106 in the same way that carriage 18 is mounted on base member 16, as described above. Thus, as with carriage 18, carriage 108 is adapted to slide back and forth in the coronal plane along the length of base member 106 while preventing transverse movement of the carriage relative to the base member. As in apparatus 10 illustrated in FIGS. 1-5, a heel wedge 114 is affixed to the end of carriage 108 adjacent support member 104 for rearwardly and laterally supporting heel H. Carriage straps 116, similar to straps 22, are provided for securing foot F to carriage 108, and leg straps 118, similar to straps 24, are provided for securing lower leg L to the front surface of leg support member 104.

Rather than using a hydraulic loading system, such as system 26 illustrated in FIGS. 1-5, a forwardly directed load is applied to carriage 108 by an extension spring 120 disposed between carriage 108 and a lead screw 122. A hook 124 is formed at one of spring 120 for engagement with an eye 126 attached to the forward end of carriage 108. The opposite end of spring 120 is fixed to the end of a spring scale 135 which in turn is connected to a turnbuckle 128 affixed to the adjacent end of lead screw 122. Lead screw 122 threadably engages with a nut 130 fixedly attached to an upright anchor wall 132 extending upwardly from the end of base member 106 opposite support member 104. A hand wheel 134 is attached to the forward end of lead screw 122 for manual rotation of the lead screw.

The operation of apparatus 110 is essentially the same as the operation of apparatus 10 illustrated in FIGS. 1-5, except that heel H is loaded by spring 120 rather than by a hydraulic loading system. Ideally, spring 120 is designed to exert a maximum predetermined force on heel H to thereby avoid excessively loading the ankle joint. Also, scale 135 provides a visual indication of the precise load applied to heel H.

From the above description, it is clear that apparatus 100 also provides all of the advantages provided by apparatus 10 including the capability of applying a precise, predetermined, forwardly directed load in the coronal plane to assist in the X-ray examination of injuries to a patient's talo-fibular ligament. Moreover, X-ray examination of the ankle area is accomplished without exposing the operator to X-rays.

As will be apparent to those skilled in the art to which the invention is addressed, the present invention may be embodied in forms and embodiments other than those specifically disclosed above, without departing from the spirit or essential characteristics of the invention. The particular embodiments of the apparatuses 10 and 100, described above, are therefore to be considered in all respects as illustrative and not restrictive, i.e. the scope of the present invention is as set forth in the appended claims rather than limited to the examples of the apparatuses 10 and 100 as set forth in the foregoing description.

I claim:

1. An apparatus for facilitating X-ray examinations of joints interconnecting first and second body members, said apparatus comprising:
(a) a support member;
(b) first securing means for securing the first body member to said support member;
(c) a carriage for supporting the second body member for movement relative to said first body member, said carriage adapted for movement transversely toward and away from said support member;
(d) second securing means for securing the second body member to said carriage; and
(e) force generating means for selectively applying a predetermined force on said carriage in a direction away from said support member to displace the second body member in a direction away from the first body member at said joint to be examined.

2. The apparatus according to claim 1, wherein said carriage includes a bed for supporting the second body member, and a wedge member at one end of said bed contacting the portion of said second body member adjacent to the jont to be examined to carry said second body member with said carriage in a direction transversely away from said support member.

3. The apparatus according to claim 1, further comprising guideway means for guiding said carriage for movement transversely toward and away from said support member.

4. The apparatus according to claim 3, wherein said guideway means includes:
(a) an elongate base member disposed perpendicularly to said support member; and
(b) roller means journaled to said carriage and engageable with said base member for antifrictional movement of said carriage toward and away from said support member.

5. The apparatus according to claim 1 or 4, wherein said force generating means includes spring means having opposite attaching portions, one of said attaching portions being connectable to said carriage and the other of said attaching portions being connectable to adjustable advance-retract means for selectively loading said spring to impose a force on said carriage in a direction away from said support member.

6. The apparatus according to claim 3, wherein said guideway means includes:
an elongate, generally planar base member extending generally perpendicular to said support member;
a pair of elongate, parallel slots formed along the side portions of either said carriage or said base member;
a pair of elongate, parallel flange members formed along the side edge portions of the other of said carriage or base member to closely engage within said cooperating slot to support said carriage for sliding movement along the length of said base member while preventing movement of said carriage in directions transverse to the length of said base member.

7. The apparatus according to claim 6 further comprising roller means joined to said carriage flange members to engage with portions of said base member slots for antifrictional movement of said carriage along said base member.

8. The apparatus according to claim 1 or 6, wherein said force generating means includes:
an elongate, tubular member extending transversely to said support member in a direction generally parallel to the line of travel of said carriage;
a piston fixed to said carriage to slide within said tubular member during movement of said carriage transversely toward and away from said support member;
working fluid within said force generating means; and,
pressure generating means to force said working fluid into said tubular member to push said piston along said tubular member to thus force said carriage away from said support member.

9. The apparatus according to claim 8, wherein said force generating means further includes an expandable bladder disposed within said tubular member and connected in fluid flow communication with said pressure generating means, said bladder enlargeable by said working fluid to press portions of said bladder against said piston when forcing said carriage away from said support member.

10. The apparatus according to claim 9, further comprising gauge means for measuring the pressure of said working fluid within said bladder.

11. An apparatus for facilitating X-ray examinations of ankle injuries, comprising:
(a) a lower leg support member;
(b) first securing means for securing the lower leg adjacent the ankle to be examined to said support member;
(c) foot support means disposed adjacent one end of said lower leg support member to grip the foot adjacent the ankle to be examined, including a heel receiving member and second securing means for securing the foot thereto;
(d) guideway means for guiding said foot support means for movement away from said leg support member; and
(e) force generating means for selectively applying a force to said foot support means in a direction away from said leg support member to move said foot support means away from said leg support member.

12. The apparatus according to claim 11, wherein:
said foot support means includes an elongate, generally planar bed for supporting the bottom of a foot;
said guideway means includes an elongate, generally planar base member fixed relative to and extending transversely to said support member, and roller means journaled on said bed and engageable with said base member for supporting and guiding said foot support means for movement away from said support member.

13. The apparatus according to claim 11, wherein:
said foot support means includes an elongate generally planar bed for supporting the underside of a foot; and
said guideway means includes an elongate, generally planar base member fixed relative to and disposed transversely to the length of said leg support member, slot means formed along the side edge portions of either said bed or said base member, and flange means extending along the side edge portions of the other of said bed or base member for closely engaging within said slots to support and guide said foot support means for sliding movement along the length of said base member while preventing movement of said foot support means in directions transversely to the length of said base member.

14. The apparatus according to claim 11, wherein said force generating means includes:
an anchor member fixed to said guideway means at a location distal from said support member; and
spring means having first and second attachment portions, with said first attachment portion being connectable to said foot support means and said second attachment portion being connectable to advance-retract means, said advance-retract means being adjustably engageable with said anchor means to maintain a selective load on said spring.

15. The apparatus according to claim 11, wherein said force generating means comprises:
a cylinder extending transversely outwardly from said lower leg support member in a direction generally parallel to the direction of movement of said foot support means;
a piston disposed longitudinally of said foot support means for sliding engagement within said cylinder; and
pressure generating means for pressurizing said cylinder to push against said piston to force said foot support means away from said support member.

16. The apparatus according to claim 15, wherein:
said force generating means further includes an expandable bladder disposed within said cylinder; and
said pressure generating means pressurizes said bladder to enlarge said bladder to press against said piston when forcing said foot support means away from said support member.

17. The apparatus according to claim 15 or 16, wherein said force generating means includes gauge means for measuring the load imposed on said foot support means by said force generating means.

18. An apparatus for facilitating X-ray examinations of ankle injuries, comprising:
(a) an elongate tibia support member;
(b) first securing means for securing the portion of the tibia adjacent the ankle to be examined to said tibia support member;
(c) foot support means disposed adjacent to one end of said tibia support member to grip the foot of the ankle to be examined, said foot support means including a wedge member for contacting against the rear of the talus;
(d) guideway means for guiding said foot support means for movement away from said tibia support member; and
(e) force generating means for selectively applying of force to said foot support means in the coronal plane in a direction away from said tibia support member to move the talus forwardly away from said tibia to thereby test whether the anterior talo-tibial ligament has ruptured.

* * * * *

UNITED STATES PATENT OFFICE
CERTIFICATE OF CORRECTION

Patent No. 4,320,749   Dated March 23, 1982

Inventor(s)  Robert D. Highley

It is certified that error appears in the above-identified patent and that said Letters Patent are hereby corrected as shown below:

Column 3, line 26, change "alignment" to -- ligament -- .

Column 3, line 66, change "artifrictionally" to -- anti-frictionally -- .

Column 4, line 44, change "illustrted" to -- illustrated -- .

Column 4, line 50, change "all" to -- wall -- .

Column 4, line 53, after "side" insert -- edge -- .

Column 5, line 35, change "52" to -- 53 -- .

Column 5, line 59, change "56" to -- 57 -- .

Column 6, line 57, change "illustratd" to -- illustrated -- .

Column 7, line 13, after "one" insert -- end -- .

Column 8, line 7, change "jont" to -- joint -- .

Column 8, line 33, change "perpendicular" to -- perpendicularly --

Signed and Sealed this

Twenty-ninth Day of June 1982

[SEAL]

Attest:

Attesting Officer

GERALD J. MOSSINGHOFF

Commissioner of Patents and Trademarks